United States Patent [19]

Duembgen et al.

[11] Patent Number: 4,595,778

[45] Date of Patent: Jun. 17, 1986

[54] PREPARATION OF METHACRYLIC ACID AND CATALYST THEREFOR

[75] Inventors: Gerd Duembgen, Dannstadt-Schauernheim; Gerd Fouquet, Neustadt; Richard Krabetz, Kirchheim; Franz Merger, Frankenthal; Friedbert Nees, Stutensee, all of Fed. Rep. of Germany

[73] Assignee: BASF Aktiengesellschaft, Ludwigshafen, Fed. Rep. of Germany

[21] Appl. No.: 587,118

[22] Filed: Mar. 7, 1984

[30] Foreign Application Priority Data

Mar. 11, 1983 [DE] Fed. Rep. of Germany ....... 3308625

[51] Int. Cl.$^4$ .................. C07C 51/235; C07C 67/08
[52] U.S. Cl. .................... 560/208; 562/535; 203/DIG. 21
[58] Field of Search ................. 562/535, 532; 560/208

[56] References Cited

U.S. PATENT DOCUMENTS

| | | | |
|---|---|---|---|
| 3,772,381 | 11/1973 | Nakamura et al. | 560/208 |
| 3,997,600 | 12/1976 | Ferlazzo et al. | 560/208 |
| 4,223,161 | 9/1980 | Shaw et al. | 562/535 |
| 4,335,018 | 6/1981 | Franz et al. | 502/209 |
| 4,458,088 | 7/1984 | Hardman et al. | 560/205 |

FOREIGN PATENT DOCUMENTS

| | | |
|---|---|---|
| 10429 | 4/1980 | European Pat. Off. |
| 1473035 | 5/1977 | United Kingdom |
| 2001256 | 1/1979 | United Kingdom |
| 2046252 | 11/1980 | United Kingdom |

*Primary Examiner*—Natalie Trousof
*Assistant Examiner*—L. Hendriksen
*Attorney, Agent, or Firm*—Oblon, Fisher, Spivak, McClelland & Maier

[57] ABSTRACT

Oxidation catalysts of the general formula $$W_6Mo_aV_bP_cCu_dAs_eSb_fX_gY_hO_x$$

where X is K, Rb and/or Cs, Y is Nb, Fe, Mn, Sn, Li, Na, Sr, Rh, Ce, Ti and/or Cr, a is from 2.0 to 6, b is from 0 to 3, c is from 0.1 to 3, d is from 0.01 to 1, e is from 0 to 1, f is from 0 to 2, g is from 0.01 to 3, h is from 0 to 1 and x is the number of oxygen atoms formally required to saturate the valencies of the catalyst components, give high conversions and particularly high selectivity in the oxidation of methacrolein in the gas phase to methacrylic acid.

10 Claims, No Drawings

PREPARATION OF METHACRYLIC ACID AND CATALYST THEREFOR

BACKGROUND OF THE INVENTION

1. Field of the Invention

A large number of oxidation catalysts have been suggested, and their use for the preparation of methacrylic acid by gas-phase oxidation of methacrolein has been proposed. However, these catalysts satisfy only some, if any, of the requirements for industrial operation in respect of formation of a small amount of by-products, in particular of acetic acid, maleic acid and citraconic acid, coupled with a technically reasonable size for the catalyst particles and high space velocities with respect to methacrolein.

2. Description of the Prior Art

U.S. Pat. No. 3,772,381 discloses, for example, catalysts which contain Mo, Cu, P, Sb and Cs and/or Ca, but, in the formation of methacrylic acid, these catalysts give an unsatisfactory selectivity of 76% at a methacrolein conversion of 75%. German Laid-Open Application DOS No. 2,523,757 proposes catalysts which, in addition to Mo, Cu and P, contain one or more alkali metals and one or more metals selected from the group comprising Sb, V, W, Fe, Mn and Sn. Although long-term operation with these catalysts results in methacrolein conversions as high as 91.5% and selectivities of 82%, the low space velocity of 1000 h$^{-1}$ and the relatively high temperatures of 325° C. and higher are unsatisfactory for industrial operation. Oxidation catalysts which are of the type disclosed in British Patent No. 2,046,252 and contain Mo, P and V and may or may not contain As and Cu or other cationic elements also exhibit high catalytic activity, but only for sizes of the catalyst particles of less than 2 mm which are not relevant industrially, and at a relatively high temperature of 330° C. Oxidation catalysts which are prepared in the presence of a high chloride ion concentration of about 1-5 equivalents per equivalent of molybdenum, for example the catalysts which contain Mo, P and W and are described in European Patent No. 00 10 429, or those which contain Mo, P and Sb and may or may not contain W and are described in U.S. Pat. No. 3,965,163, exhibit relatively good catalytic activity during short operating times; however, catalysts of this type which have a long life and are sufficiently selective are difficult to prepare in a reproducible manner. Furthermore, the stated catalysts have a tendency to form larger amounts of acetic acid when they are used in industrially reasonable particle sizes of 3 mm or more. British Patent No. 2,001,256 discloses other oxidic catalysts which contain Mo, P, As, Cu and Cr and are prepared in the presence or absence of a dibasic carboxylic acid, hydroxycarboxylic acid, mannitol or pyrogallol as a reducing agent. However, the properties of these catalysts and of the abovementioned ones are generally unsatisfactory when the raw material used for the preparation of methacrylic acid is methacrolein which has been prepared by condensation of propanol with formaldehyde. As a result of the preparation process, this methacrolein is contaminated with unreacted propanol as well as organic amines, dimers of methacrolein and methyl pentenal. Even small amounts of these impurities generally result in a reduction in the performance of such catalysts.

SUMMARY OF THE INVENTION

The particularly useful present invention provides oxidation catalysts, for the oxidation of methacrolein to methacrylic acid in the gas phase. When industrial-grade methacrolein is used along with a catalyst having a particle size conventionally used in industrial fixed-bed reactors is employed, high yields and the formation of only small amounts of by-products are ensured coupled with high space velocities over long operating times.

DESCRIPTION OF THE INVENTION

This invention provides oxidation catalysts of the formula

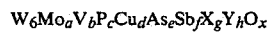

$$W_6Mo_aV_bP_cCu_dAs_eSb_fX_gY_hO_x$$

where X is K, Rb and/or Cs, Y is Nb, Fe, Mn, Sn, Li, Na, Sr, Rh, Ce, Ti and/or Cr, a is from 2.0 to 6, b is from 0 to 3, c is from 0.1 to 3, d is from 0.01 to 1, e is from 0 to 1, f is from 0 to 2, g is from 0.01 to 3, h is from 0 to 1, and x is the number of oxygen atoms formally required to saturate the valencies of the other components.

For formal reasons, any NH$_4^+$ ions which may be present have been omitted from the formula. The catalysts may also contain other components in amounts determined by the composition of the raw materials used.

With regard to the composition, preferred oxidation catalysts of the above formula are those in which a is from 4.0 to 5.9, b is from 0.1 to 2, c is from 0.5 to 1.5, d is from 0.05 to 0.5, e is from 0.01 to 0.5, f is from 0.01 to 1.5, g is from 0.05 to 1.5 and h is from 0 to 0.5. Among the components of group Y, Ti, Sn and/or Rh are preferred, if appropriate in combination with another component from this group.

The catalysts are generally prepared as follows: compounds of the individual components in an aqueous medium, ie. in aqueous solution or suspension, are combined under conditions which lead to the formation of phosphorus-containing heteropolyacids of molybdenum and tungsten or their salts, and the product is then dried and molded, and is finally advantageously activated by calcination at elevated temperatures.

Examples of suitable sources of molybdenum and tungsten are molybdic acid, ammonium molybdate, phosphomolybdic acid and its ammonium salt, tungstic acid, ammonium tungstate, and phosphotungstic acid and its ammonium salt. Although other compounds can also be used, the stated compounds are preferred, in particular phosphotungstic acid as a source of tungsten, and ammonium molybdate, molybdic acid and phosphomolybdic acid as a source of molybdenum. Arsenic is advantageously used in the form of the oxide or acid or as the ammonium salt of the acids. Suitable sources of phosphorus are the abovementioned heteropolyacids as well as various compounds; however, phosphoric acid and its ammonium salts are preferred. The elements of groups X and Y, and Cu and Sb, can be used in the form of, for example, the oxides, carbonates, nitrates, chlorides, fluorides, formates, oxalates or acetates, but are preferably employed in the form of the salts of low molecular weight mono- and dicarboxylic acids. It is generally advantageous if reductive organic substances, in particular low molecular weight monocarboxylic acids, eg. formic acid or acetic acid, di- and hydroxycarboxylic acids, eg. oxalic acid, tartaric acid or citric acid, or their salts, preferably formic acid alone or in combination with one of the above acids, in particular acetic acid, are present in the starting solution and during the preparation. The carboxylic acids can be added in amounts of from 0.02 to 2, preferably from 0.05 to 1.5, moles per mole of tungsten. In contrast, relatively high chloride ion concentration can result in damage to the catalyst in some cases. Hence, the amount of chloride ions in the starting solution should preferably be below 0.3, in particular below 0.25, mole per mole of molybdenum.

The components can be combined at room temperature or at elevated temperature. For example, the aqueous solutions or suspensions of molybdic acid, phosphoric acid, arsenic acid, antimony(III) oxide and copper oxide or a copper salt can be mixed, and the mixture then refluxed, for example for from 2 to 24 hours. In another embodiment, the aqueous solutions of water-soluble compounds of the components, eg. ammonium heptamolybdate, diammonium phosphate, diammonium arsenate or arsenic acid, and antimony trichloride, are mixed together at room temperature in a solution containing hydrochloric acid or, preferably, formic acid, tartaric acid, succinic acid or citric acid, the mixture is combined with an aqueous solution of, for example, phosphotungstic acid, the additional cationic components are added, and water is removed from the product at elevated temperatures.

Dehydration or drying of the aqueous suspension of the components is carried out in general by evaporation in stirred kettles at below 140° C., or by spray drying at outlet temperatures of from 80° to 140° C.

The resulting materials are dried and then usually milled to a particle size of from 200 to 1200 μm, a conventional carrier, such as $SiO_2$ or an alumina, and, if required, a lubricant such as graphite, may be added, and the materials are then molded to spheres, tablets, rings or other shapes. Calcination or activation can then be effected in a gentle stream of air, nitrogen or a mildly reducing gas at from 180° to 400° C., preferably from 220° to 380° C., in particular from 320° to 360° C. The carrier materials may also be added during the evaporation of the catalyst suspension, with the result that the catalyst components are deposited on the carrier. Finally, the dried and milled catalyst material can be calcined at the stated temperature without the addition of a carrier, and the product can then be converted to moldings or can be applied onto carriers, in particular spherical carriers, in the form of bowls, in a conventional manner, for example by the methods disclosed in U.S. Pat. Nos. 4,305,843 and 4,297,247. After calcination, the active catalytic materials all have the structure of a distorted heteropolyacid or its salts, and exhibit characteristic X-ray diffraction lines. They are particularly suitable for the oxidation of methacrolein to methacrylic acid in the gas phase under conventional conditions, particularly when the starting material used is methacrolein which has been prepared by condensation of formaldehyde with propionaldehyde.

In the gas-phase oxidation of methacrolein, the oxidizing agent used is a mixture of oxygen and steam, this gas mixture generally being passed over a fixed-bed catalyst. In general, the pressures employed are from 1 to 5, advantageously from 1 to 2.5, bar. In the process, the residence time for the methacrolein-containing gas mixture is generally from 0.5 to 5 sec. under standard conditions, residence times of from 1 to 4 sec. at from 200° to 340° C., in particular 220° to 320° C., being preferred. In addition to oxygen, methacrolein and steam, the reaction gases generally contain inert gases, in particular nitrogen; the oxygen is generally fed in as air, but pure oxygen may also be used. Furthermore, the reaction gas generally contains oxides of carbon, particularly when, after isolation of the methacrylic acid formed, residual exit gas from the reaction is recycled as a diluent, together with unreacted methacrolein, to the oxidation reaction. In the reaction gas, the molar ratio methacrolein:oxygen:steam:inert gas is generally 1:(1–6):(1–20):(4–50), preferably 1:(1.5–4):(2–10):(6–30). The methacrylic acid is isolated from the hot exit gases from the reaction in a conventional manner, in general by rapid cooling with water.

The methacrolein can have been obtained by various methods, for example by gas-phase oxidation of tert.-butyl alcohol, isobutylene or $C_4$ mixtures or by condensation of propionaldehyde wth formaldehyde. The use of the novel catalysts is particularly advantageous when the methacrolein used has been prepared by condensation of propionaldehyde with formaldehyde in the presence of a salt of a secondary amine, or with an aminal in the presence of an acid in aqueous solution. Industrial-grade products obtained in this manner are generally 94–99% pure and contain, in addition to unreacted propionaldehyde, small amounts of organic amines, such as diethylamine or diethanolamine, methylpentenal and dimers of methacrolein. The stated purities are based on crude anhydrous methacrolein, but crude methacrolein can contain as much as 3.5% by weight of water. If unreacted methacrolein and uncondensed exit gases from the reaction are recycled to the oxidation reaction, the gas mixture for the synthesis may also contain small amounts of readily volatile by-products, such as oxides of carbon or acrolein.

When the process is carried out industrially, a tube-bundle reaction is generally used, the catalyst being present in the reactor in the form of a fixed bed. To avoid localized superheating, the catalyst activity can be modified so that it increases continuously or stepwise in the direction of flow of the reaction gases. This can be achieved by, for example, diluting the catalyst with less active or inactive catalyst moldings or carrier moldings, or by using 2 or more catalysts having different activities and/or selectivities. The novel oxidation of methacrolein to methacrylic acid can also be carried out using a fluidized-bed catalyst, but fixed-bed catalysts are preferred.

In working up the reaction gases, the latter may also be cooled indirectly before being washed, for example with water; the working up stage generally gives aqueous soutions of methacrylic acid which may furthermore contain small amounts of acetic acid, maleic acid and acrylic acid. The methacrylic acid can be obtained from the resulting, for example aqueous, solution by extraction with a suitable solvent, eg. methyl methacrylate, in a conventional manner, and can be either esterified directly with an alkanol, in particular methanol, or subjected to distillation to isolate it from the extract and separate it from by-products. The unreacted methacrolein can be distilled off from the aqueous condensate or, for example, expelled with steam, and can be recycled to the oxidation reaction.

The novel catalysts also exhibit high activity and selectivity in other oxidation reactions, for example in the oxidation of acrolein to acrylic acid or of substituted toluene derivatives to substituted benzaldehydes and benzoic acids.

In the examples which follow, the methacrolein used is 97-99% pure and contains water and propionaldehyde as well as small amounts of secondary amines and by-products of the synthesis of methacrolein from propionaldehyde and formaldehyde. In the examples, parts and percentages are by weight, unless otherwise stated. Parts by volume bear the same relation to parts by weight as that of the liter to the kilogram.

EXAMPLES

Example 1

A solution of 6.1 parts of diammonium phosphate and 2.6 parts of diarsenic pentoxide in 100 parts by volume of water, 3.5 parts of ammonium metavanadate and 0.38 part of diammonium phosphate in 300 parts of water, 4.5 parts of antimony(III) chloride in a mixture of 6 parts by volume of formic acid and 20 parts by volume of water, a solution of 5.0 parts of copper(II) acetate in 100 parts by volume of water and 10.1 parts of potassium nitrate in 150 parts of water are added in succession to an aqueous solution of 97.2 parts of ammonium heptamolybdate in 600 parts by volume of water. The suspension is evaporated down on a water bath at about 85° C., after which the dry material is milled to a particle size smaller than 1.2 mm, 2% of graphite powder is added, and the mixture is pressed to give 3×3 mm tablets. The moldings are then calcined for 6 hours at 355° C. to give a catalyst having the following composition:

$$W_6Mo_{5.5}V_{0.3}P_1As_{0.2}Sb_{0.2}Cu_{0.25}K_1O_x$$

80 parts by volume of catalyst tablets are introduced into a reaction tube which has a diameter of 16 mm and is heated in a salt bath. A gas mixture consisting of 3.3 vol % of methacrolein, 9.1 vol % of oxygen, 29.5 vol % of steam and 58.1 vol % of nitrogen is passed over the catalyst at a space velocity of 1320 h$^{-1}$. At a bath temperature of 310° C., the conversion is 85.3 mole %, and the selectivities with respect to methacrylic acid and acetic acid are 88 mole % and 2.6 mole % respectively. A total amount of 0.8%, based on the amount of methacrylic acid, of maleic acid and citraconic acid is formed.

COMPARATIVE EXPERIMENTS (1A) A catalyst is prepared as described in Example 1 except that the addition of potassium nitrate is omitted. Under the test conditions of Example 1 and at a bath temperature of 310° C., the conversion is 69.9 mole %, and the selectivities with respect to methacrylic acid and acetic acid are 82.5 mole % and 3.7 mole % respectively. Maleic acid and citraconic acid are formed in a total amount of 1.2%.

(1B) In a further comparative experiment, a catalyst having the composition $Mo_{10}V_1P_1As_{0.2}Cu_{0.25}K_{0.1}O_x$ is prepared as described in Example CE 16 of German Laid-Open Application DOS No. 3,010,434. The catalyst is molded to 3×3 mm tablets, and is tested as described in Example 1, under the test conditions stated in that Example. At a bath temperature of 324° C., the conversion is 85.2 mole %, and the selectivities with respect to methacrylic acid and acetic acid are 74.4 mole % and 8.6 mole % respectively. Maleic acid and citraconic acid are formed in a total amount of 2.2%.

(1C) A catalyst is prepared as described in Example 1, except that Mo is completely replaced by the same molar amount of W (composition: $W_{11.5}V_{0.3}P_1As_{0.2}Sb_{0.2}Cu_{0.25}K_1O_x$). Under the test conditions of Example 1, the conversion is 53.6 mole %, and the selectivities with respect to methacrylic acid and acetic acid are 67.2 mole % and 12.2 mole % respectively. Maleic acid and citraconic acid are obtained in a total amount of 1.4%.

Example 2

Example 1 is repeated, with the difference that a gas mixture consisting of 6.3 vol % of methacrolein, 11.8 vol % of oxygen, 22 vol % of steam and 59.9 vol % of nitrogen is passed over 80 parts by volume of catalyst at a space velocity of 1100 h$^{-1}$. At a bath temperature of 294° C., the conversion is 62 mole %, and the selectivities with respect to methacrylic acid and acetic acid are 90.1 mole % and 1.9 mole % respectively. Maleic acid and citraconic acid are formed in an amount of 0.9%, based on methacrylic acid.

After an operating time of 90 days, and at the same bath temperature, the conversion is 59.5 mole %, and the selectivities with respect to methacrylic acid and acetic acid are 90.8 mole % and 1.1 mole % respectively. Maleic acid and citraconic acid are formed in a total amount of 0.82%.

Example 3

A catalyst having the composition $W_6Mo_{5.8}P_1As_{0.2}Sb_{0.2}Cu_{0.25}K_{0.2}O_x$ is prepared by the method described in Example 1, and is tested under the test conditions stated in that example. At a bath temperature of 294° C., the conversion is 85.6 mole %, and the selectivities with respect to methacrylic acid and acetic acid are 85.7 mole % and 3.0 mole % respectively.

COMPARATIVE EXPERIMENTS (3A) A catalyst is prepared using the general method of preparation described in Example 3, but without the addition of potassium nitrate and with a larger amount of molybdenum. The resulting catalyst corresponds to the formula $W_6Mo_{6.4}P_1As_{0.2}Cu_{0.25}O_x$. Under the test conditions of Example 3 and at a bath temperature of 306° C., the conversion is 67.2 mole %, and the selectivities with respect to methacrylic acid and acetic acid are 81.7 mole % and 5.1 mole % respectively. Maleic acid and citraconic acid are formed in a total amount of 1.8%.

(3B) With a catalyst having the composition $W_2Mo_{10}P_1As_{0.2}Sb_{0.2}Cu_{0.25}O_x$, and at a bath temperature of 294° C., the conversion is 86.4 mole %, and the selectivities with respect to methacrylic acid and acetic acid are 80.9 mole % and 5.2 mole % respectively.

Example 4

A catalyst of the general formula $W_6Mo_{5.8}V_{0.6}P_1As_{0.2}Sb_{0.2}Cu_{0.25}K_1O_x$ is prepared as described in Example 1. 80 parts by volume of the calcined catalyst tablets are tested at a bath temperature of 316° C., under the conditions stated in Example 2. The conversion is 63.5 mole %, and the selectivities with respect to methacrylic acid and acetic acid are 90.3 mole % and 2.7 mole % respectively. Maleic acid and citraconic acid are formed in a total amount of 0.62%.

Examples 5 to 14

Further catalysts are prepared using the method described in Example 1, with the difference that additional components are introduced or the proportions of the components are changed. The catalysts are tested under the test conditions described in Example 2, and their compositions are summarized in the Table below. The additional components are introduced in the following forms: manganese(II) acetate tetrahydrate, iron(II) oxalate, niobium pentoxide, ammonium chromate, anatase, tin(II) oxide, rubidium nitrate, cesium nitrate, lithium hydroxide, sodium hydroxide, rhodium(III) chloride hydrate and cerium nitrate. The catalysts have virtually the same activity as the catalyst described in Example 1. The conversions and the selectivities with respect to methacrylic acid, each in mole %, and the bath temperatures are summarized in the Table below. The selectivity with respect to acetic acid is less than 3 mole % in each case, and the amount of maleic acid and citraconic acid together is less than 0.7%, based on the amount of methacrylic acid.

TABLE

| Example | Catalyst | Bath temperature °C. | Conversion | Selectivity |
|---|---|---|---|---|
| 5 | $W_6Mo_{5.8}V_{0.3}P_1As_{0.2}Sb_{0.2}Cu_{0.25}Os_1Na_{0.01}$ | 294 | 56 | 90.1 |
| 6 | $W_6Mo_{5.8}V_{0.3}P_1As_{0.2}Sb_{0.2}Cu_{0.25}Rb_{0.5}Li_{0.01}$ | 294 | 61 | 88.5 |
| 7 | $W_6Mo_{5.8}V_{0.3}P_1As_{0.2}Sb_{0.2}Cu_{0.25}K_1Ti_{0.2}$ | 287 | 61.7 | 88 |
| 8 | $W_6Mo_{5.8}V_{0.3}P_1As_{0.2}Sb_{0.2}Cu_{0.25}K_1Rh_{0.1}$ | 286 | 61.5 | 86.1 |
| 9 | $W_6Mo_{5.8}V_{0.3}P_1As_{0.2}Sb_{1.0}Cu_{0.25}K_1Ce_{0.05}$ | 292 | 59.4 | 88.0 |
| 10 | $W_6Mo_{5.8}V_{0.3}P_{1.1}As_{0.3}Sb_{0.2}Cu_{0.25}Sr_{0.1}K_{0.8}$ | 288 | 62.0 | 90.5 |
| 11 | $W_6Mo_{5.8}V_{0.3}P_1As_{0.2}Sb_{0.2}Cu_{0.25}K_1Fe_{0.05}$ | 294 | 59.3 | 87.0 |
| 12 | $W_6Mo_{5.8}V_{0.3}P_1As_{0.2}Sb_{0.2}Cu_{0.2}K_{0.2}Mn_{0.05}$ | 294 | 55 | 89.3 |
| 13 | $W_6Mo_{5.8}V_{0.3}P_1As_{0.2}Sb_{0.2}Cu_{0.25}K_{1.1}Sn_{0.05}$ | 292 | 63.1 | 87.2 |
| 14 | $W_6Mo_{5.8}V_{0.3}P_1As_{0.2}Sb_{0.2}Cu_{0.2}Cr_{0.05}K_{0.2}Nb_{0.2}$ | 305 | 58 | 88.2 |

Example 15

A catalyst of the general formula $W_6Mo_4W_{0.3}P_1As_{0.3}Sb_{0.25}Cu_{0.3}Cs_{0.8}O_x$ is prepared by the procedure described in Example 1, and is tested under the conditions stated in Example 2. At a bath temperature of 324° C., the conversion is 54.5 mole %, and the selectivities with respect to the methacrylic acid and acetic acid are 85.5 mole % and 2.7 mole % respectively. Maleic acid and citraconic acid are formed in a total amount of 0.85%, based on the methacrylic acid.

We claim:

1. In a process for the preparation of methacrylic acid comprising:
   (a) reacting methacrolein with a gas mixture containing oxygen and steam, at from 200° to 340° C., over a catalyst which contains molybdenum, tungsten, antimony and phosphorus, and
   (b) separating the methacrylic acid from the reaction gases wherein the improvement is that the catalyst of step (a) is an oxidation catalyst of the formula

   $W_6Mo_aV_bP_cCu_dAs_eSb_fX_gY_hO_x$ wherein
   X is selected from the group consisting of K, Rb, and Cs,
   Y is selected from the group consisting of Nb, Fe, Mn, Sn, Li, Na, Sr, Rh, Ce, Ti and Cr,
   a is from about 4.0 to 5.9,
   b is from about 0.1 to 2,
   c is from about 0.5 to 1.5,
   d is from about 0.05 to 0.5,
   e is from about 0.01 to 0.5,
   f is from about 0.01 to 1.5,
   g is from about 0.05 to 1.5, and
   h is from about 0 to 0.5.

2. The process of claim 1 wherein step (a) is carried out under the following conditions:
   (1) a pressure of between about 1 to 5 bar:
   (2) a temperature of between about 200° to 340° C.; and
   (3) for a period of between about 1 to 4 sec.

3. The process of claim 1 wherein the gas mixture further comprises nitrogen gas.

4. The process of claim 1 wherein the molar ratio of methacrolein:oxygen:steam:recycled gases is about 1:(1–6):(1–20):(4–50).

5. The process of claim 1 being carried out in a tube-bundle reactor, wherein the catalyst is present in the form of a fixed bed.

6. The process of claim 5 wherein the activity of the catalyst is continuously or stepwise increased in the direction of flow of the gas mixture.

7. The process of claim 1 being carried out in a fluidized bed.

8. The process of claim 1 wherein the methacrylic acid is obtained in step (b) as an aqueous solution by rapid cooling with water.

9. The process of claim 8 further comprising:
   (c) extracting the methacrylic acid from its aqueous solution with a solvent;
   (d) esterifying the extracted methacrylic acid with an alkanol; and
   (e) separating the esterified methacrylic acid from the solvent and by-products.

10. The process of claim 9 wherein the separation step (e) is carried out by distillation.

* * * * *